(12) United States Patent
Marcu et al.

(10) Patent No.: US 8,089,625 B2
(45) Date of Patent: Jan. 3, 2012

(54) TIME-RESOLVED AND WAVELENGTH-RESOLVED SPECTROSCOPY FOR CHARACTERIZING BIOLOGICAL MATERIALS

(75) Inventors: Laura Marcu, Davis, CA (US); Javier A. Jo, College Station, TX (US); Daniel Elson, London (GB)

(73) Assignee: The Regents of the University of California, Oakland, CA (US)

( * ) Notice: Subject to any disclaimer, the term of this patent is extended or adjusted under 35 U.S.C. 154(b) by 241 days.

(21) Appl. No.: 12/516,341

(22) PCT Filed: Nov. 26, 2007

(86) PCT No.: PCT/US2007/085530
§ 371 (c)(1),
(2), (4) Date: May 26, 2009

(87) PCT Pub. No.: WO2008/127434
PCT Pub. Date: Oct. 23, 2008

(65) Prior Publication Data
US 2010/0067003 A1    Mar. 18, 2010

Related U.S. Application Data

(60) Provisional application No. 60/861,662, filed on Nov. 28, 2006.

(51) Int. Cl.
*G01J 3/30* (2006.01)

(52) U.S. Cl. .................................................... 356/318
(58) Field of Classification Search .......... 356/317–318, 356/417
See application file for complete search history.

(56) References Cited

U.S. PATENT DOCUMENTS

| | | | | |
|---|---|---|---|---|
| 5,828,452 A | * | 10/1998 | Gillispie et al. | ............... 356/318 |
| 7,576,844 B2 | * | 8/2009 | Hairston et al. | ............... 356/417 |
| 2004/0007675 A1 | * | 1/2004 | Gillispie et al. | ............ 250/458.1 |

* cited by examiner

*Primary Examiner* — Kara E Geisel
(74) *Attorney, Agent, or Firm* — Park, Vaughan, Fleming & Dowler LLP; Laxman Sahasrabuddhe

(57) ABSTRACT

One embodiment of the present invention provides a system that characterizes a biological sample by analyzing light emissions from the biological sample in response to an excitation. The system first radiates the biological sample with a laser impulse to cause the biological sample to produce a responsive light emission. Next, the system uses a wavelength splitting device to split the responsive light emission into a set of spectral bands of different central wavelengths. The system applies temporal delays to the set of spectral bands so that each spectral band arrives at an optical detector at a different time, thereby allowing the optical detector to temporally resolve the responsive light emission for each spectral band separately. Next, the system captures the delayed spectral bands within a single detection window of the optical detector. The system then processes the captured spectral bands.

28 Claims, 4 Drawing Sheets

TIME-RESOLVED AND WAVELENGTH-RESOLVED SPECTROSCOPY FOR CHARACTERIZING BIOLOGICAL MATERIALS

GOVERNMENT LICENSE RIGHTS

This invention was made with United States Government support under Grant No. HL067377 awarded by the National Institutes of Health. The Government has certain rights in this invention.

BACKGROUND

1. Field of the Invention

The present invention relates to techniques for characterizing biological materials through analyzing laser-induced light emissions. More specifically, the present invention relates to a method and apparatus for characterizing biological materials by performing a time-resolved and wavelength-resolved analysis on laser-induced fluorescence emissions from the biological materials.

2. Related Art

Laser-induced emission spectroscopy, in particular, a laser-induced fluorescence spectroscopy (LIFS) has been extensively applied to complex biological systems to diagnose human diseases, such as tumors or atherosclerotic plaques in the medical field, and to analyze chemical or biochemical composition of organic matters in other fields. The increased interest in LIFS can be attributed to its noninvasive approach to obtain both qualitative and quantitative information of a biological system in vivo. In comparison to other spectroscopic techniques, LIFS provides several advantages, such as wavelength tunability, narrow bandwidth excitation, directivity, and short pulses excitation. Furthermore, LIFS can selectively and efficiently excite the fluorophores in organic matter and greatly improves the fluorescence selectivity and detectability.

Typically during an LIFS process, a sample is excited with a short pulse of light of a predetermined wavelength and intensity, and a reemission profile is measured following the excitation using a fast photodetector. LIFS measurements can be categorized as either static (i.e., steady-state or time-integrated) or dynamic (time-resolved). Typically, steady-state techniques provide an "integral" spectrum over time, which contains such information as fluorescence emission intensity, spectral distribution, and polarization/anisotropy. However, while using the steady-state systems, the time-dependence of emission and the potential information contained therein are ignored.

On the other hand, time-resolved techniques allow real-time evolution of the laser-induced emission to be directly recorded, which was made possible by the availability of short (nanoseconds) and ultra-short (picoseconds) pulsed lasers, as well as advances in high-speed electronics. Because the light emission process occurs in a very short time interval after the stimulating event (e.g., fluorescence decay time is in the order of nanoseconds), the time-resolved measurement can provide rich information about molecular species and protein structures of the sample. For example, the time-resolved techniques permit "early" processes (typically the direct excitation of short-lived states or very rapid subsequent reactions) and "late" processes (typically from long-lived states, delayed excitation by persisting electron populations or by reactions which follow the original electron process) to be "separated" in the measured data.

More importantly, the time-resolved measurement can be complemented by spectral information in the laser-induced emission to reveal additional characteristics of a sample. Note that the time-resolved measurement only obtains an integrated effect from a wide range of wavelengths. To resolve the laser-induced emission into component wavelengths while still being able to perform time-resolved measurement, some existing LIFS techniques use a scanning monochromator to select wavelengths from the broadband emission one wavelength at a time, and to direct the selected wavelength component to the photodetector. However, to resolve another wavelength from the emission spectrum, the sample has to be excited again to produce another reemission, while the monochromator is tuned to select the new wavelength.

Unfortunately, these existing techniques can take a significant amount of time to resolve multiple spectral components from a wide band light emission. Although each wavelength component can be recorded in real-time, the transition time of using a monochromator to select another wavelength can take up to a few seconds, which becomes the limiting factor in performing real-time measurements. Furthermore, an overall measurement can take a large amount of time if a large number of stimulation locations on the sample have to be measured.

Hence, what is needed is a method and an apparatus that facilitates near real-time recording of both time-resolved and wavelength-resolved information from a light emission caused by a single excitation of a sample.

SUMMARY

One embodiment of the present invention provides a system that characterizes a biological sample by analyzing light emissions from the biological sample in response to an excitation. The system first radiates the biological sample with a laser impulse to cause the biological sample to produce a responsive light emission. Next, the system uses a wavelength-splitting device to split the responsive light emission into a set of spectral bands of different central wavelengths. The system then applies temporal delays to the set of spectral bands so that each spectral band arrives at an optical detector at a different time, thereby allowing the optical detector to temporally resolve the responsive light emission for each spectral band separately. Next, the system captures the delayed spectral bands within a single detection window of the optical detector. The system then processes the captured spectral bands.

In a variation on this embodiment, the system applies a temporal delay to a spectral band by: coupling the spectral band into a delay device; allowing the spectral band to travel through the delay device; and receiving the spectral band from the output of the delay device, wherein the delay device introduces a controlled temporal delay to the spectral band while traveling through the delay device.

In a further variation on this embodiment, the delay device is an optical fiber with a predetermined length.

In a further variation, the controlled temporal delay is determined by the properties of the optical fiber and the length of the optical fiber.

In a variation on this embodiment, the system splits the responsive light emission into the set of spectral bands by: dividing the responsive light emission into spectral bands using a first stage of a wavelength splitting device; and if necessary, subdividing one or more spectral bands using a second stage of a wavelength splitting device.

In a further variation, prior to splitting the responsive light emission, the system collects the responsive light emission using an optical fiber. Next, the system directs the collected responsive light emission onto the first stage of the wavelength splitting device.

In a further variation on this embodiment, the output of the first stage of the wavelength splitting device can be coupled to the input of the second stage of the wavelength splitting device through a direct coupling or an optical fiber coupling.

In a variation on this embodiment, the system splits the responsive light emission into the set of spectral bands by using multiple stages of a wavelength splitting device.

In a further variation, the wavelength splitting device can include: a dichroic filter cube; a dichroic prism; a dichroic mirror; a diffraction grating; an acousto-optic modulator; or any other wavelength splitter devices.

In a variation on this embodiment, the responsive light emission is a fluorescence decay of the biological sample caused by the laser impulse excitation.

In a further variation on this embodiment, the temporal delay between adjacent spectral bands is sufficiently long to temporally separate the fluorescence decay profile of each of the spectral bands.

In a variation on this embodiment, the optical detector is a photomultiplier tube (PMT).

In a further variation on this embodiment, the PMT is a gated PMT which provides a detection window sufficiently wide to capture the set of spectral bands.

In a variation on this embodiment, the apparatus additionally includes an optical bandpass filter configured to further refine a spectral band.

DETAILED DESCRIPTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the claims.

TIME-RESOLVED, WAVELENGTH-RESOLVED SYSTEM OVERVIEW

Figure 1:
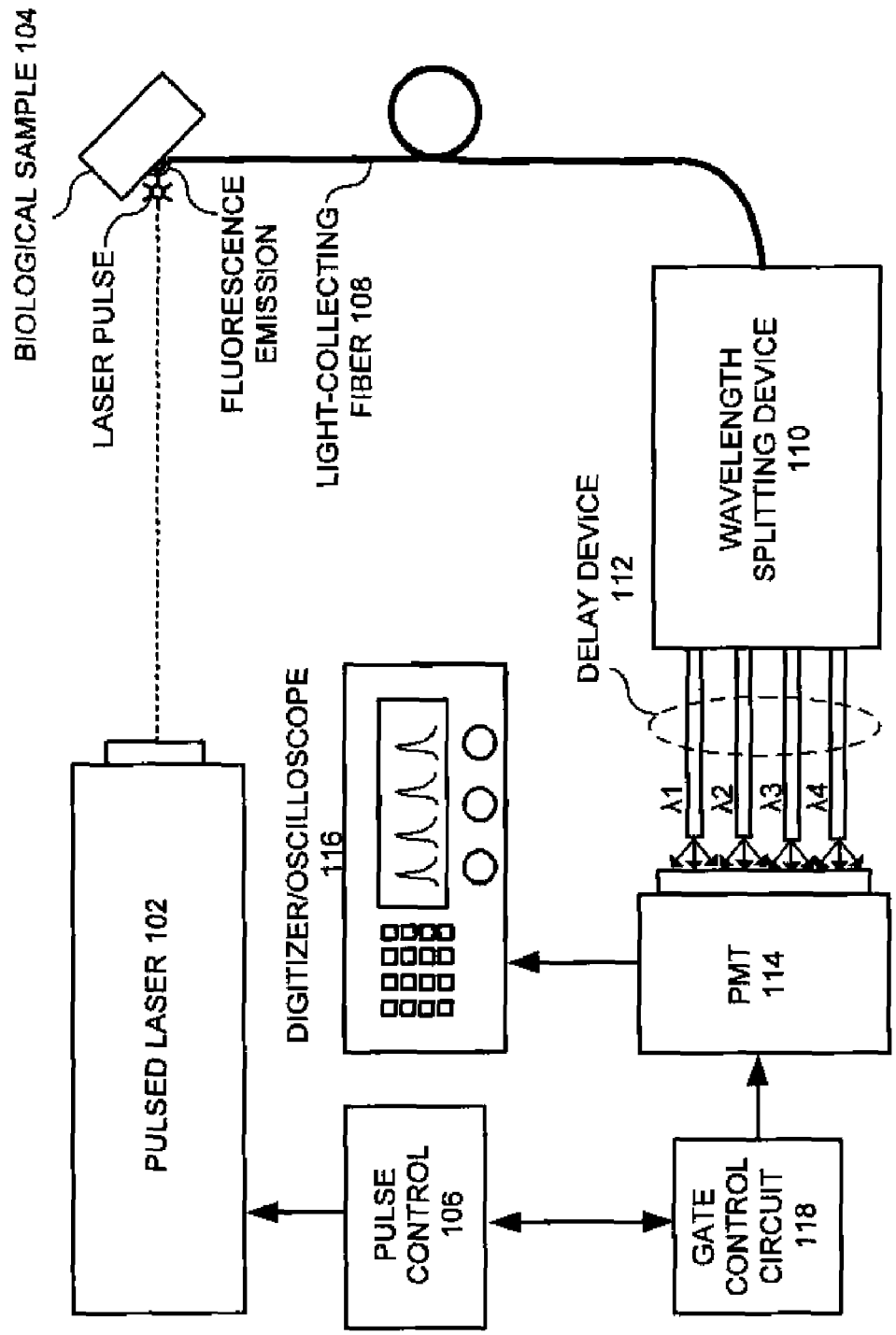
FIG. 1 illustrates a block diagram of a time-resolved, wavelength-resolved measurement system for analyzing a laser-induced emission in accordance with an embodiment of the present invention.

FIG. 1 illustrates a block diagram of a time-resolved, wavelength-resolved measurement system for analyzing a laser-induced emission in accordance with an embodiment of the present invention.

The excitation source is a pulsed laser 102. Output pulses from pulsed laser 102 radiate upon a biological sample 104 at a predetermined wavelength and power level suitable for exciting biological sample 104 without causing damage to the sample. Specifically, pulse laser 102 is controlled by a pulse controller 106, which provides precise timing to each laser impulse output. In one embodiment of the present invention, pulsed laser 102 emits ultraviolet (UV) light pulses to excite biological sample 104. Note that the laser emission from pulsed laser 102 can be focused into an optical fiber, and guided to a specific location on biological sample 104 through the optical fiber.

Laser-impulse excitation causes biological sample 104 to produce a responsive light emission, such as a fluorescence emission, which typically has a wide spectrum comprising many wavelengths. This laser-induced light emission is then collected by a light-collecting fiber 108. In one embodiment of the present invention, light-collecting fiber 108 is a multi-mode fiber.

Light-collecting fiber 108 then brings the wide band emission light into a wavelength-splitting device 110, which can comprise one or more wavelength-splitting stages.

Next, the wide band emission light undergoes a series of wavelength splitting processes so that the wide band signal can be resolved into a number of narrow spectral bands, each with a distinct central wavelength (e.g., $\lambda_1$, $\lambda_2$, $\lambda_3$, and $\lambda_4$, etc.)

Next, the wavelength-resolved spectral bands are coupled into corresponding delay device 112, which applies a predetermined temporal delay to each spectral band as it travels towards a photodetector.

The temporally-delayed spectral bands exiting delay device 112 are arranged onto a fast-response photomultiplier tube (PMT) 114 so that the fluorescence decay profile of each wavelength-resolved spectral band can be individually recorded and temporally resolved. Note that the delays applied to these spectral bands allow each optical signal to arrive at PMT 114 at a different time, which allows the decay profile of each spectral band detected by the PMT separately. Next, the output from PMT 114 can be recorded and displayed using a high-speed digitizer/oscilloscope 116.

In one embodiment of the present invention, PMT 114 is a gated PMT controlled by a gate control circuit 118, so that PMT 114 only responds to light signals during a narrow detection window when PMT 114 is open. In one embodiment of the present invention, gate control circuit 118 and pulse control 106 are synchronized so that all the fluorescence decay profiles associated with a single laser-induced excitation may be recorded within a single PMT detection window. Note that besides using a PMT, other photodetectors may be used.

WAVELENGTH SPLITTING DEVICE

Figure 2:
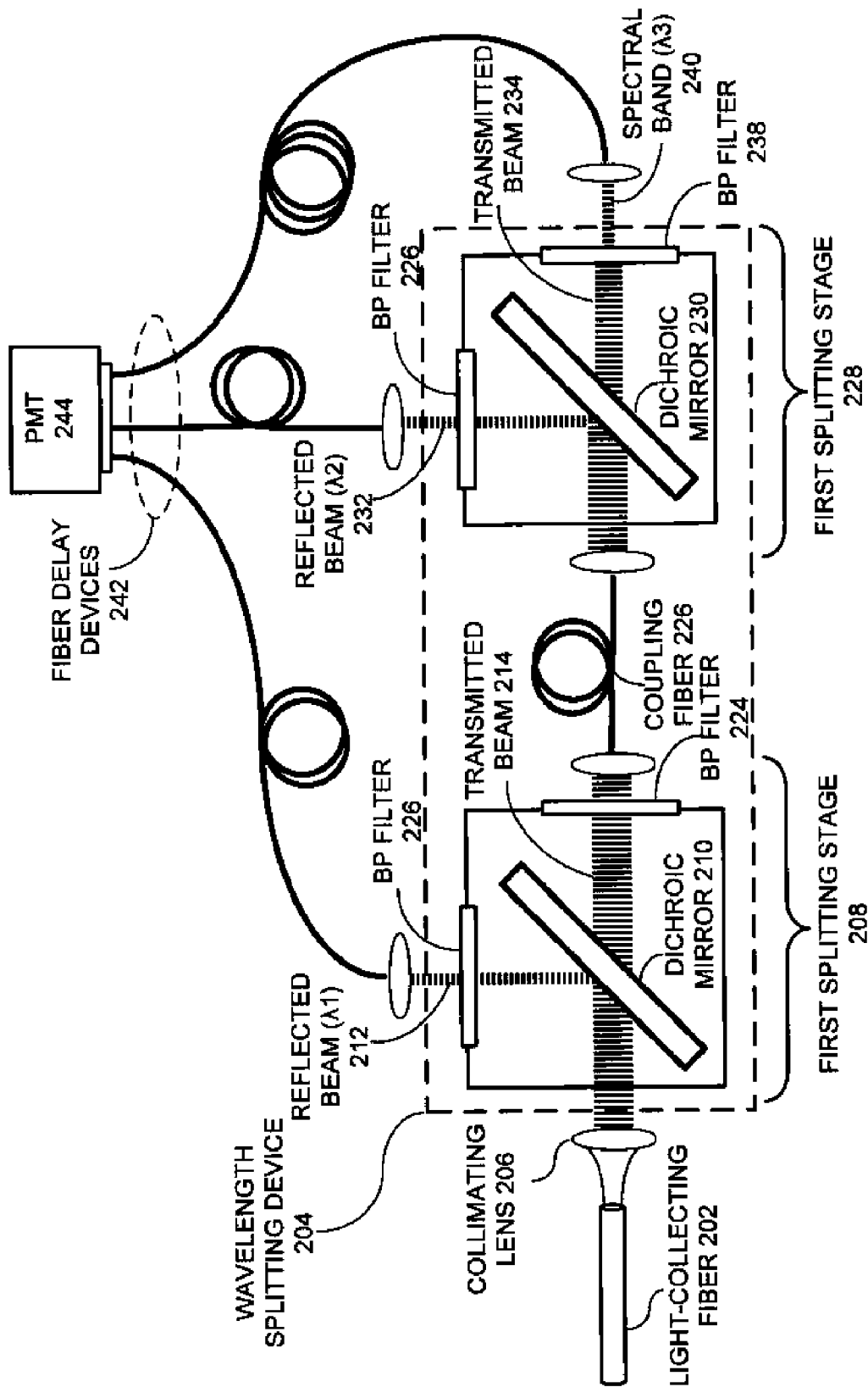
FIG. 2 illustrates a wavelength splitting device in accordance with an embodiment of the present invention.

FIG. 2 illustrates a wavelength splitting device in accordance with an embodiment of the present invention.

As is shown in FIG. 2, laser-induced light emission (containing a wide range of wavelengths) from the biological sample is collected by a light-collecting fiber 202, which brings the emission light towards wavelength-splitting device 204. Upon exiting light-collection fiber 202 and before entering wavelength splitting device 204, the emission light is first collimated using a collimating lens 206. Collimating lens 206 can include, but is not limited to, a Gradient Index (GRIN) lens, or an aspheric lens. Next, the collimated light beam is directed onto first splitting stage 208 of wavelength-splitting device 204.

Note that first splitting stage 208 comprises a dichroic mirror 210 in the path of the incoming wide band beam. Upon interacting with dichroic mirror 210, the incoming beam is split into two beams: a reflected beam 212 and a transmitted beam 214. In this embodiment, reflected beam 212 contains a narrow spectral band with a central wavelength of $\lambda_1$, while transmitted beam 214 is a wide band beam containing the remainder of the emission spectrum. Note that an alternative configuration of dichroic mirror 210 allows the transmitted beam to be a narrow spectral band beam and the reflected beam to be a wide band beam.

First splitting stage 208 can additionally include optical bandpass filters 224 and 226, which can be used to further narrow the spectral bands of reflected beam 212 and transmitted beam 214. However, in one embodiment of the present invention, one or both of bandpass filters 224 and 226 are not included in first splitting stage 208.

In a variation of this embodiment, dichroic mirror 210 is replaced with a beam splitter. The beam splitter can divide the incoming light beam in two beams, wherein each beam carries a fraction (in power) of the full spectrum of the original light beam without causing wavelength splitting. To select a desired spectral band from each of the full band beam, optical bandpass filters 224 and 226 are used in a configuration similar to FIG. 2.

Upon exiting first splitting stage 208, transmitted beam 224 which contains majority of the emission spectrum is collected by coupling fiber 226, and is then collimated and directed into a second splitting stage 228. In this embodiment, second splitting stage 228 has a substantially identical configuration as first splitting stage 208, and hence includes a dichroic mirror 230 which splits the incoming beam into a reflected beam 232 and a transmitted beam 234. Note that reflected beam 232 has a narrow spectral band with a central wavelength of $\lambda_2$, while transmitted beam 234 contains the remainder of the emission spectrum. Reflected beam 232 then passes through an optical bandpass filter 236 upon exiting wavelength splitting device 204, which allows the narrow spectral band of beam 232 to be further refined.

Transmitted beam 234 passes through an optical bandpass filter 238, which selects a narrow spectral band 240 with a central wavelength of $\lambda_3$. Note that if bandpass filter 238 is not included, transmitted beam 234 can be further split into more individual narrow spectral bands. This can be accomplished by adding one or more splitting stages similar to the first and the second stage. This modular design facilitates adding and removing splitting stages based on how many spectral bands need to be resolved from the original wide band emission signal. Note that each type of biological sample is generally associated with a different set of characteristic wavelengths to be resolved.

Upon exiting wavelength splitting device 204, narrow spectral band signals 212, 232, and 240 are coupled into corresponding delay devices 242. In this embodiment, each delay device is an optical fiber with a predetermined length which is determined by the temporal delay required for each signal while traveling to PMT 244. More detail of the delay device is provided below.

Figure 3:
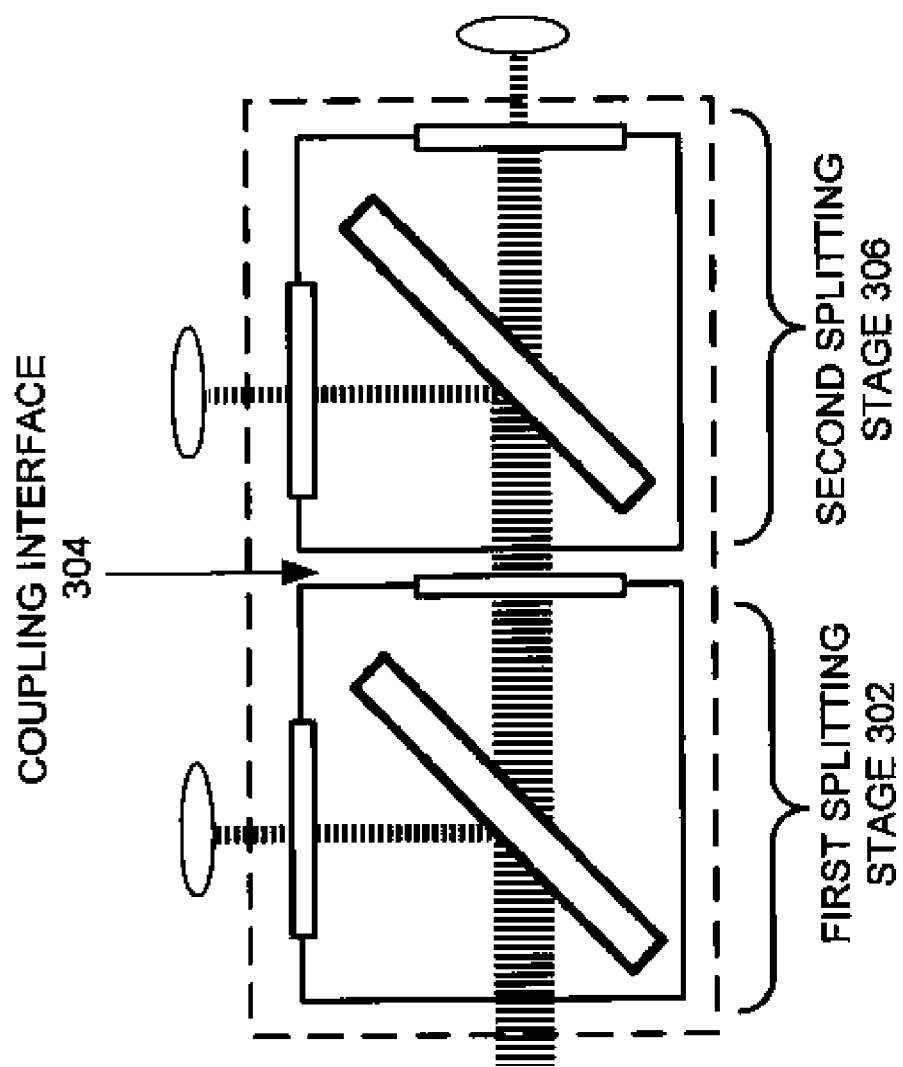
FIG. 3 illustrates a variation of the wavelength splitting device in FIG. 2 in accordance with an embodiment of the present invention.

FIG. 3 illustrates a variation of the wavelength splitting device in FIG. 2 in accordance with an embodiment of the present invention.

In FIG. 2, the coupling between first splitting stage 208 and second splitting stage 228 involves using a coupling fiber 226, which has two coupling interfaces (one from the first stage to the coupling fiber and the other from the coupling fiber to the second stage). However, in FIG. 3, the coupling fiber is removed and the beam exiting from first splitting stage 302 passes through a narrow gap interface 304 between the two stages and enters second splitting stage 306 directly. Because this coupling scheme involves only one coupling interface, the attenuation can be reduced in comparison to the implementation illustrated in FIG. 2. It also allows a more compact design for the wavelength splitting device.

Figure 4:
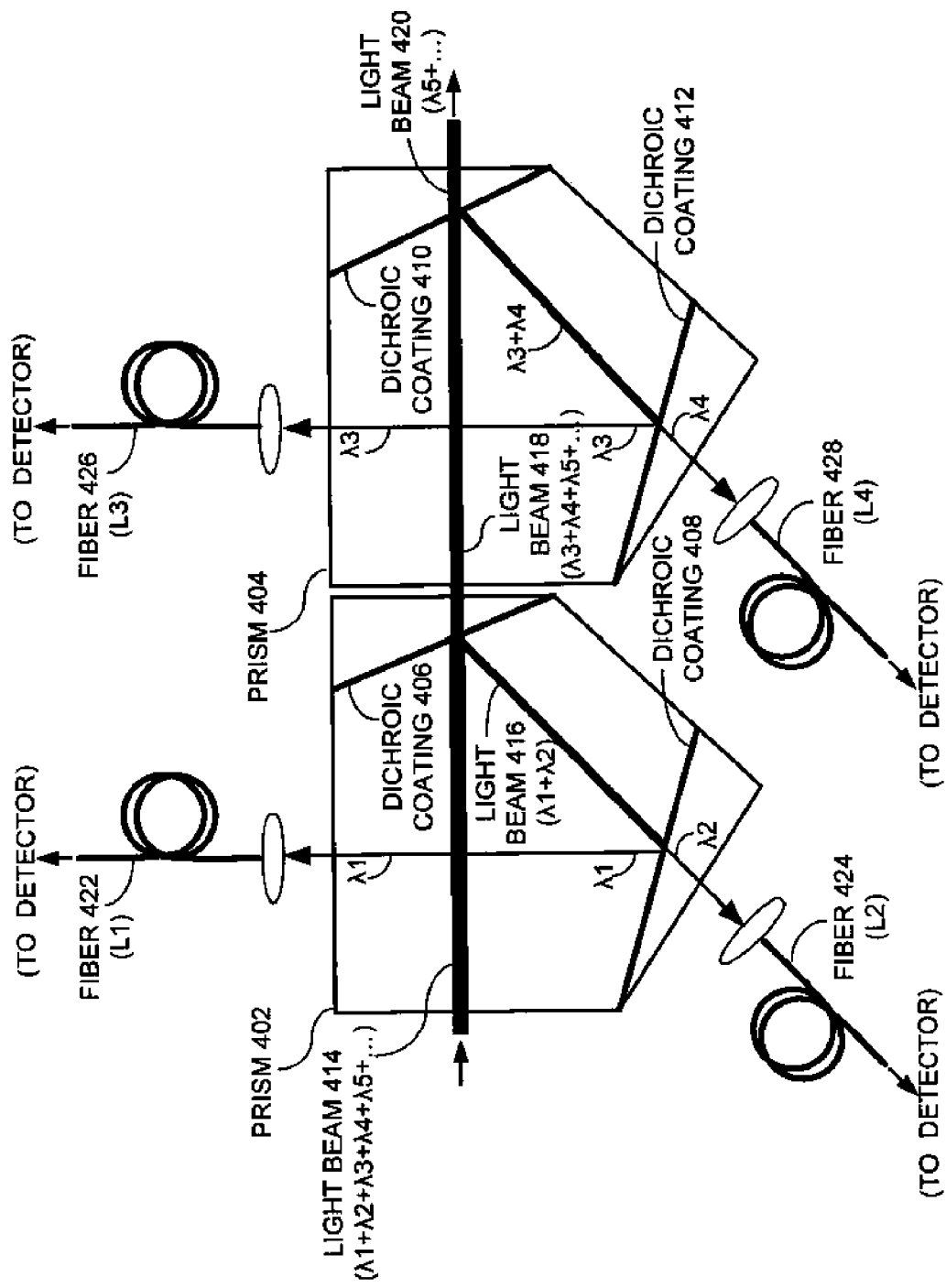
FIG. 4 illustrates a wavelength splitting device which uses dichroic prism beam splitters in accordance with an embodiment of the present invention.

FIG. 4 illustrates a wavelength splitting device which uses dichroic prism beam splitters in accordance with an embodiment of the present invention.

Similar to the device in FIG. 2, wavelength splitting device in FIG. 4 comprises two wavelength splitting stages. However, each of the two splitting stages comprises a beam splitting prism instead of a dichroic mirror. Note that each of the two beam splitting prisms 402 and 404 further comprises two dichroic coating interfaces. For example, prism 402 includes dichroic coating interfaces 406 and 408, and prism 404 includes dichroic coating interfaces 410 and 412. Each dichroic coating interface in the prism serves as a wavelength selector to select a particular spectral band from a wide emission spectrum and transmit or reflect the rest of the spectrum.

As illustrated in FIG. 4, a wide band light beam 414 enters prism 402, wherein light beam 414 includes a large number of narrow spectral bands with central wavelengths of $\lambda_1$, $\lambda_2$, $\lambda_3$, $\lambda_4$, $\lambda_5$, etc. Light beam 414 first impinges on dichroic coating interface 406 which reflects off a light beam 416 containing spectral bands $\lambda_1$ and $\lambda_2$, and transmits light beam 418 containing rest of the spectral bands. Reflected light beam 416 then impinges upon interface 408 which splits spectral band $\lambda_1+\lambda_2$ into two separate narrow spectral bands $\lambda_1$ and $\lambda_2$, which then exit prism 402 from the top and the bottom, respectively.

Light beam 418 travels across a narrow gap interface between prism 402 and prism 404, and subsequently enters a second beam splitting stage of prism 404. Similarly, prism 404 splits the incoming beam into three beams: a beam containing a narrow spectral band $\lambda_3$ which exits prism 404 from the top, a beam containing a narrow spectral band $\lambda_4$ which exits prism 404 from the bottom, and a beam 420 containing the remaining spectrum $\lambda_5+\ldots$, which exits prism 408 from the right. Note that, an optical bandpass filter can be optionally placed in the path of beam 420 to select a particular spectral band, for example, spectral band $\lambda_5$, and block the rest of the spectrum. In this embodiment, the two wavelength splitting stages can generate five distinct narrow spectral bands of interest. In comparison to using dichroic mirrors in FIG. 2, using the beam splitting prisms allows more efficient wavelength division. Note that although not shown in FIG. 4, each resolved spectral band can be further refined with an optical bandpass filter before being coupled into a corresponding delay device.

Note that wavelength splitting device in FIG. 4 is modular, which enables it to be extended by adding one or more splitting stages to further subdivide the remaining spectrum. Depending on the number of spectral bands that need to be resolved, one can select the appropriate number of beam splitting stages and number of resolved spectral bands per splitting stage. In one embodiment of the present invention, heterogeneous splitting stages can be combined. For example, a dichroic mirror can be used in one stage and a beam splitting prism can be used in another stage.

Note that although we have described wavelength splitting in the context of using dichroic filters and optical bandpass filters, the concept of using modularized stages for beam splitting/spectral band selection is not limited to the specific devices and configurations described herein. For example, other types of wavelength splitting devices can include a diffraction grating or an acousto-optic modulator.

TEMPORAL DELAY AND TIME-RESOLVED DETECTION

As seen in FIG. 4, each resolved wavelength component from the wavelength-splitting device is coupled to a corresponding delay device and subsequently undergoes a predetermined amount of delay in the corresponding delay device. In this embodiment, the delay devices are optical fibers 422, 424, 426, and 428 with different lengths $L_1$, $L_2$, $L_3$, and $L_4$, respectively. More specifically, to temporally separate each of the four wavelength components $\lambda_1$, $\lambda_2$, $\lambda_3$, and $\lambda_4$ at the same optical detector, each of the wavelength component travels through a different length of optical fiber, and thereby experiences a different amount of delay. Eventually, each of the wavelength components arrives at the optical detector at different time which enables each component to be detected separately.

Note that the length of the optical fiber is not the only determining factor for the delay. Other physical properties of the optical fiber, including, but is not limited to, the refractive index of the fiber are also used to determine the length of the fiber to achieve a specified amount of delay.

Because in the time-domain, each spectral component has a decay profile that lasts for a specific amount of time (e.g., tens of nanoseconds), the temporal delay between two adjacent spectral components can be designed to be sufficiently long to temporally separate the two decay profiles.

In one embodiment of the present invention, the optical detector is a gated PMT which only responds to incoming light signals within a short detection window controlled by a gate control circuit. This gated window can be designed to be sufficiently long so that all the resolved and temporally separated wavelength components will arrive at the PMT within the gated window. Hence, the gated PMT can capture all wavelength components which are caused by a single laser induced-emission within one detecting window.

Note that although we have described an optical delay mechanism which is implemented using optical fibers, the delay device which is used to temporally separate the resolved spectral bands is not limited to optical fibers, and any delay device can generally be used.

CONCLUSION

The present invention improves the speed of data acquisition by allowing all of the time-resolved and wavelength-resolved data from a single laser excitation to be recorded in a single detection window. More specifically, the fluorescence decay resulting from a single laser-impulse excitation in a biological sample is first wavelength-resolved into spectral bands. Next, the spectral bands are temporally separated by using a different length of optical fiber to delay each of the spectral bands. The temporally separated spectral bands are then recorded using a fast optical detector within a single detection window, hence facilitating simultaneous time and wavelength resolution.

The data acquisition speed is improved because no monochromator or spectrometer is required, which was a limiting factor in data acquisition time for prior art systems. This is achieved by replacing a monochromator with modularized wavelength-splitting stages. More specifically, the wavelength-splitting technique of the present invention selects spectral bands by using specific dichroic coatings, which allows each splitting stage to be easily customized for a specific biological sample to detect a desired spectral band.

The ability of the system to provide fast data acquisition and analysis on biological samples enables near real-time display of diagnostic information of tissues and human diseases, such as tumors or atherosclerotic plaques.

The foregoing descriptions of embodiments of the present invention have been presented only for purposes of illustration and description. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

What is claimed is:

1. A method for characterizing a biological sample by analyzing light emissions from the biological sample in response to an excitation, the method comprising:
   radiating the biological sample with a laser impulse to cause the biological sample to produce a responsive light emission;
   splitting the responsive light emission into a set of spectral bands of different central wavelengths;
   applying temporal delays to the set of spectral bands so that each spectral band arrives at an optical detector at a different time, thereby allowing the optical detector to temporally resolve the responsive light emission for each spectral band separately;
   capturing the set of delayed spectral bands within a timing-controlled single detection window of the optical detector; and
   processing the captured spectral bands.

2. The method of claim 1, wherein applying a temporal delay to a spectral band involves:
   coupling the spectral band into a delay device;
   allowing the spectral band to travel through the delay device; and
   receiving the spectral band from the output of the delay device, wherein the delay device introduces a controlled temporal delay to the spectral band while traveling through the delay device.

3. The method of claim 2, wherein the delay device is an optical fiber with a predetermined length.

4. The method of claim 3, wherein the controlled temporal delay is determined by the properties of the optical fiber and the length of the optical fiber.

5. The method of claim 1, wherein splitting the responsive light emission into the set of spectral bands involves:
   dividing the responsive light emission into spectral bands using a first stage of a wavelength splitting device; and
   if necessary, subdividing one or more spectral bands using a second stage of a wavelength splitting device.

6. The method of claim 5, wherein prior to splitting the responsive light emission, the method further comprising:
   collecting the responsive light emission in an optical fiber; and
   directing the collected responsive light emission onto the first stage of the wavelength splitting device.

7. The method of claim 5, wherein an output of the first stage of the wavelength splitting device can be coupled to an input of the second stage of the wavelength splitting device through:
   a direct coupling; or
   an optical fiber coupling.

8. The method of claim 1, wherein splitting the responsive light emission into the set of spectral bands involves using multiple stages of a wavelength splitting device.

9. The method of claim 5, wherein the wavelength splitting device can include:
   a dichroic filter cube;
   a dichroic prism;

a dichroic mirror;
a diffraction grating;
an acousto-optic modulator; or
any other wavelength splitter devices.

10. The method of claim 1, wherein the responsive light emission is a fluorescence decay of the biological sample caused by the laser impulse excitation.

11. The method of claim 10, wherein the temporal delay between adjacent spectral bands is sufficiently long to temporally separate the fluorescence decay profile of each of the spectral bands.

12. The method of claim 1, wherein the optical detector is a photomultiplier tube (PMT).

13. The method of claim 12, wherein the PMT is a gated PMT which provides a detection window sufficiently wide to capture the set of spectral bands.

14. The method of claim 1, wherein a spectral band is further refined with an optical bandpass filter.

15. A system for characterizing a biological sample by analyzing light emissions from the biological sample in response to an excitation, comprising:
    a pulsed laser configured to radiate the biological sample with a laser impulse to cause the biological sample to produce a responsive light emission;
    a wavelength-splitting mechanism configured to split the responsive light emission into a set of spectral bands of different central wavelengths;
    a temporal-delay mechanism configured to apply temporal delays to the set of spectral bands so that each spectral band arrives at an optical detector at a different time, thereby allowing the optical detector to temporally resolve the responsive light emission for each spectral band separately;
    a detection mechanism configured to capture the set of delayed spectral bands within a timing-controlled single detection window of the optical detector; and
    a processing mechanism configured to process the captured spectral bands.

16. The system of claim 15, wherein the temporal-delay mechanism is configured to:
    couple the spectral band into a delay device;
    allow the spectral band to travel through the delay device; and to
    receive the spectral band from the output of the delay device, wherein the delay device introduces a controlled temporal delay to the spectral band while traveling through the delay device.

17. The system of claim 16, wherein the delay device is an optical fiber with a predetermined length.

18. The system of claim 17, wherein the controlled temporal delay is determined by the properties of the optical fiber and the length of the optical fiber.

19. The system of claim 15, wherein the wavelength-splitting mechanism is configured to:
    divide the responsive light emission into spectral bands using a first stage of a wavelength splitting device; and if necessary, to
    subdivide one or more spectral bands using a second stage of a wavelength splitting device.

20. The system of claim 19, further comprises:
    a collection mechanism configured to collect the responsive light emission using an optical fiber; and
    a directing mechanism configured to direct the collected responsive light emission onto the first stage of the wavelength splitting device.

21. The system of claim 19, wherein an output of the first stage of the wavelength splitting device can be coupled to an input of the second stage of the wavelength splitting device through:
    a direct coupling; or
    an optical fiber coupling.

22. The system of claim 15, wherein the wavelength-splitting mechanism is configured to use multiple stages of a wavelength splitting device.

23. The system of claim 19, wherein the wavelength splitting device can include:
    a dichroic filter cube;
    a dichroic prism;
    a dichroic mirror;
    a diffraction grating;
    an acousto-optic modulator; or
    any other wavelength splitter devices.

24. The system of claim 15, wherein the responsive light emission is a fluorescence decay of the biological sample caused by the laser impulse excitation.

25. The system of claim 24, wherein the temporal delay between adjacent spectral bands is sufficiently long to temporally separate the fluorescence decay profile of each of the spectral bands.

26. The system of claim 15, wherein the optical detector is a photomultiplier tube (PMT).

27. The system of claim 26, wherein the PMT is a gated PMT which provides a detection window sufficiently wide to capture the set of spectral bands.

28. The system of claim 15, wherein a spectral band is further refined with an optical bandpass filter.

* * * * *